United States Patent
Fuchs

[11] Patent Number: 6,055,979
[45] Date of Patent: May 2, 2000

[54] DOSING AND DISCHARGING DEVICE FOR FLOWABLE MEDIA INCLUDING POWDER/AIR DISPERSIONS

[75] Inventor: Karl-Heinz Fuchs, Radolfzell, Germany

[73] Assignee: Ing. Erich Pfeiffer GmbH, Radolfzell, Germany

[21] Appl. No.: 08/831,100

[22] Filed: Apr. 1, 1997

[30] Foreign Application Priority Data

Apr. 2, 1996 [DE] Germany .................. 196 13 185

[51] Int. Cl.⁷ .................................................. A61M 11/00
[52] U.S. Cl. ............................ 128/203.15; 128/203.12; 128/200.21; 128/200.19; 128/203.23; 222/193; 222/189
[58] Field of Search .................... 128/203.15, 203.12, 128/203.23, 200.14, 200.23, 200.19, 200.21, 200.11; 239/490, 493; 222/193, 189, 61; 604/58

[56] References Cited

U.S. PATENT DOCUMENTS

| | | | |
|---|---|---|---|
| 1,873,260 | 8/1932 | Barce . | |
| 2,122,234 | 6/1938 | McAuliffe | 128/203.15 |
| 2,202,079 | 5/1940 | Ayres | 221/61 |
| 2,358,329 | 9/1944 | Houghton | 222/193 |
| 2,470,297 | 5/1949 | Fields | 128/203.15 |
| 2,501,047 | 3/1950 | Gustafsson et al. | 128/200.11 |
| 2,549,303 | 4/1951 | Friden | 128/203.15 |
| 2,570,774 | 10/1951 | Davis | 128/203.15 |
| 2,579,280 | 12/1951 | Trumbour et al. | 128/203.12 |
| 2,641,255 | 6/1953 | Leonaitis | 128/203.15 |
| 2,642,063 | 6/1953 | Brown | 128/203.15 |
| 3,840,184 | 10/1974 | Spivey | 239/415 |
| 4,007,858 | 2/1977 | Shay | 222/193 |
| 4,261,488 | 4/1981 | Bennett | 222/633 |
| 4,286,735 | 9/1981 | Sneider | 222/189 |
| 4,657,007 | 4/1987 | Carlin et al. | 128/200.21 |
| 4,801,093 | 1/1989 | Brunet et al. | 128/203.12 |
| 5,320,714 | 6/1994 | Brendel | 128/203.23 |
| 5,323,936 | 6/1994 | Wolter et al. | 222/401 |
| 5,341,801 | 8/1994 | Zechner | 128/203.15 |
| 5,505,193 | 4/1996 | Ballini et al. | 128/200.21 |

FOREIGN PATENT DOCUMENTS

| | | |
|---|---|---|
| 35055 | 11/1908 | Austria . |
| 0 206 012 A1 | 3/1986 | European Pat. Off. . |
| 0 111 163 B1 | 6/1987 | European Pat. Off. . |
| 0 201 701 B1 | 4/1990 | European Pat. Off. . |
| 558 018 | 8/1932 | Germany . |
| 1033147 | 6/1958 | Germany . |
| 1148769 | 5/1963 | Germany . |
| 1500167 | 4/1969 | Germany . |
| 78 00 713 | 5/1978 | Germany . |
| 87 07 725 | 5/1987 | Germany . |
| 39 01 110 A1 | 7/1990 | Germany . |
| 41 28 295 A1 | 8/1991 | Germany . |
| 42 01 665 A1 | 7/1993 | Germany . |
| 93 12 772 | 11/1993 | Germany . |
| 44 15 462 C1 | 8/1995 | Germany . |
| 674355 | 6/1952 | United Kingdom . |
| WO 88/08335 | 11/1988 | WIPO . |

OTHER PUBLICATIONS

German search report dated Dec. 5, 1996 in German Appl. No. 196 13 185.5.

*Primary Examiner*—John G. Weiss
*Assistant Examiner*—V. Srivastava
*Attorney, Agent, or Firm*—Quarles & Brady LLP

[57] ABSTRACT

A dosing device (17) for the medical administration of powder (16) through the nose or mouth has a valve body (27) which is movable in a discharge channel (22) between two valve seats (25, 26). During suction, the spherical valve body (27) is raised from the lower, container-sealing valve seat (26) and moved by a flow drag to the upper valve seat (25), so that it closes the discharge channel (22) and terminates dosing. The formation of the air/powder dispersion can be assisted in that the air subsequently sucked into the container is directed onto or into a powder supply or to a powder receiver in a pre-chamber fillable by tilting the device for pre-dosing.

12 Claims, 5 Drawing Sheets

DOSING AND DISCHARGING DEVICE FOR FLOWABLE MEDIA INCLUDING POWDER/AIR DISPERSIONS

FIELD OF USE AND PRIOR ART

The invention relates to a dosing device for flowable media, particularly in discharge apparatuses for pharmaceutical or cosmetic products, such a powder/air dispersions, the medium flowing through a discharge channel, which has a closure.

For the administration of pharmaceuticals dosing always constitutes a significant problem. The action of a product is often dependent on, or is at least improved when, administration takes place in aerosol form. Atomization takes place in air for liquid products or, with solids, in the form of a solid aerosol or a corresponding dispersion of a powder in air. Such dispersions or aerosols can be produced by discharging with pumps, it being possible in the case of liquid products to introduce the liquid directly in a finely atomized form into the ambient air, i.e. not to use the air as an atomizing medium. This is more difficult with powders, where dosing is particularly problematical.

Powder atomizing devices are known (DE 41 28 295 A), in which the powder supply is in the form of small capsules, which are "blown empty" by an air flow, so as to dispense a powder quantity as a dose. However, these devices are complicated and require a complicated packing of the individual powder capsules. It is also difficult to uniformly empty the capsules during use, so that the quantity that is discharged fluctuates within wide limits.

OBJECT OF THE INVENTION

The object of the invention is to create a dosing device of the aforementioned type in which it is possible to use a simple dosing device independent of the nature of production or preparation of the medium to be discharged.

SUMMARY OF THE INVENTION

According to the invention the closure in the discharge channel is moveable with a time lag from a starting position to a closing position under the action of the flow. Thereby, the discharge process, namely the actual flow, produces the end of the discharge. Its start is fixed by the beginning of the discharge operation.

Preferably, the closure has a closure body, which cooperates with a valve seat and can be, for example, in the form of a ball. The body can be movable through the length of a path, which movement produces a time delay. The force acting on the body and which gives rise to the movement, can be the flow resistance or drag of the flowing medium acting on the body. In such a case the closure body can be located in a discharge channel that is wider than the closure body. A rest is provided in the discharge channel for the closure body in its starting position by a second valve seat.

It is to be noted that, for atomizers, devices already exist in which a valve body cooperates, as required, with two facing valve seats. Such a construction is disclosed in European patent EP 201 701 B, assigned to the assignee of the present invention, where a valve acting in both directions is provided in the form of a suction valve, which also operates in the overhead position.

Gravity offers the simplest possibility for creating the force operating in opposition to the action produced by the flow. Gravity reversal, due to the buoyancy of the valve body, could also be used under corresponding conditions. It would also be possible to use springs or other forces, for example magnetic force, as the force directed counter to the flow action. During dosage, as a result of the flow action, the valve body is placed in motion, preferably with a force action dependent on the speed of flow. As a result, in the case of different flow rates, dosing takes place in a very uniform manner, i.e. with lower flow rates it will last longer until the closure stops the dosage, whereas dosing is terminated earlier with higher flow rates. In all cases it is possible to effectively ensure that no uncontrolled quantity can be dispensed.

It has also been found that due to the mass forces arising after initiating the movement, the setting of an equilibrium, i.e. the maintaining of the closure body in a position where it does not reach the closure, is almost excluded. If the device is dimensioned so that there is a flow rate producing the powder/air dispersion when the closure body is brought into motion, it will carry out this movement completely up to the closure.

The closure characteristics can be modified by various factors. Thus, the shape and absolute weight, as well as the specific gravity of the closure body can influence the characteristics in the same way as its relationship to the channel in which movement occurs. Thus, for example, the diameter of the channel in which the closure body moves may change to attain a desired dosing characteristic. Thus, it is possible through a relatively high force (high weight or additional loading) to maintain the rest for the closure body until a pressure suitable for producing an adequate flow has built up. A relatively large annular space is provided for flow around the valve body, so as to obtain an adequate time lag and the annular space for flow around the valve body is then reduced in cross section along the length of the channel. This assures the transfer into the closure position under all circumstances and also brings about a certain throttling prior to the end of dosing, so that the latter does not occur too suddenly. This more particularly applies in the case if, as is preferred, the dosing device is used as an inhaler, where the flow takes place by oral suction via a mouthpiece.

With such a construction, the powder to be discharged can be disposed in a container and during inhalation can be sucked up from the surface and concentrated in adequate quantity in the air. In this case the container must have a vent, so that the air can flow in.

According to another feature of the invention, the discharge of a powder/air dispersion from a powder-containing container is provided by a discharge apparatus, in which said dispersion is produced. A vent leading into the container can be directed into or onto the powder supply in the container. The air sucked in as a result of the discharge can bring about a whirling up or turbulence of the powder, to produce the dispersion. Thus, from the vent a tube is directed onto or under the powder surface, so that the subsequently sucked air brings about a planned turbulence.

The action exerted by the flow on the closure body can also be produced in other ways, for example by a vacuum in a side channel produced by the flow, so that a closure body located therein is sucked into the closure position.

The construction in which the closure body acts on a second valve seat, which closes the container in the rest position, ensures that the usually hydrophillic powder is largely sealed against the atmosphere. This can also be improved by a cap being placed over the discharge apparatus, which closes both the vent and the discharge channel and which uses a pin to keep the closure body in the rest position.

These and further features can be gathered from the claims, description and drawings and the individual features, both singly and in the form of subcombinations can be implemented in an embodiment of the invention and in other fields and can represent advantageous, independently protectable constructions for which protection is hereby claimed.

The subdivision of the application into individual sections, as well as the subtitles in no way restrict the general validity of the statements made under them.

BRIEF DESCRIPTION OF THE DRAWINGS

An embodiment of the invention is described in greater detail hereinafter relative to the attached drawings, in which.

DESCRIPTION OF PREFERRED EMBODIMENTS

Figure 1:
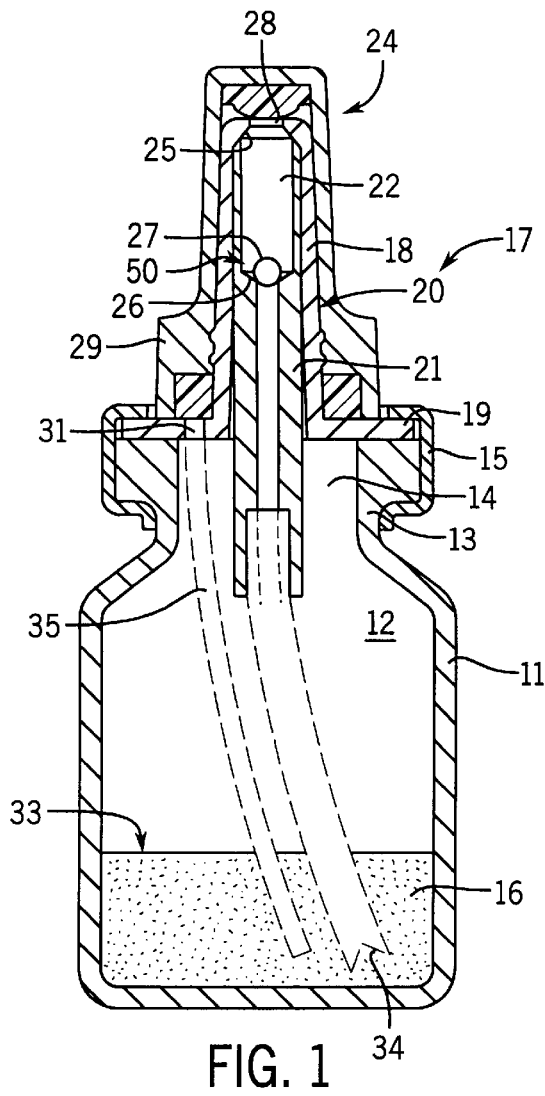
FIG. 1 is a vertical section through a powder inhaler with a dosing device of the invention in the starting position.
Figure 2:
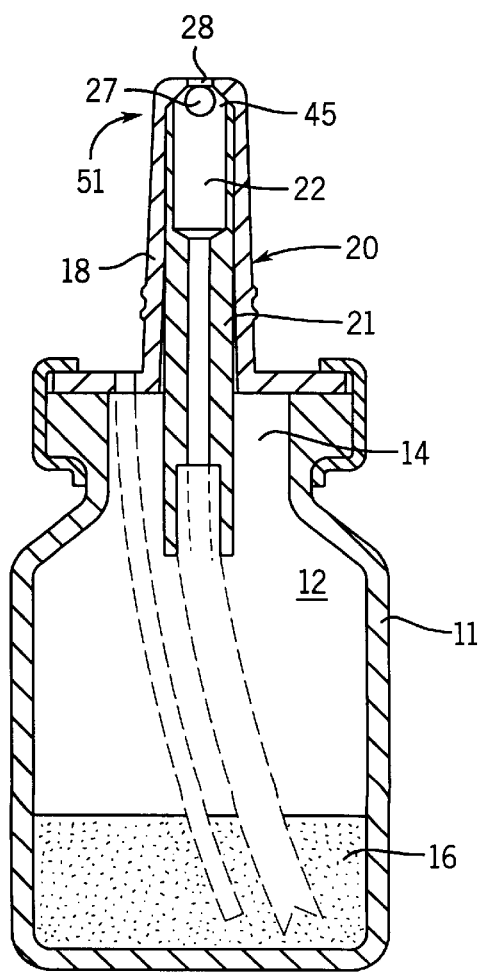
FIG. 2 is a vertical section view dosing device according to FIG. 1 in its closed position.

FIGS. 1 and 2 show a dosing device 17 fitted to a container 11, in whose interior 12 is provided a supply of a powder 16, by means of a crimped closure 15, which engages over a flange 19 of the dosing device casing 20. The container can be a normal bottle with a neck 13 and an opening 14, but other container configurations are also possible.

The dosing device 17 has a mouthpiece 18 extending upward from the flange 19, for insertion into a body opening, such as a nostril or the mouth, to exert a suction action. At its upper end mouthpiece 18 has an aperture 28, at which terminates a discharge channel 22, which is located in an insert 21, which is pressed into the casing 20.

Figure 1A:
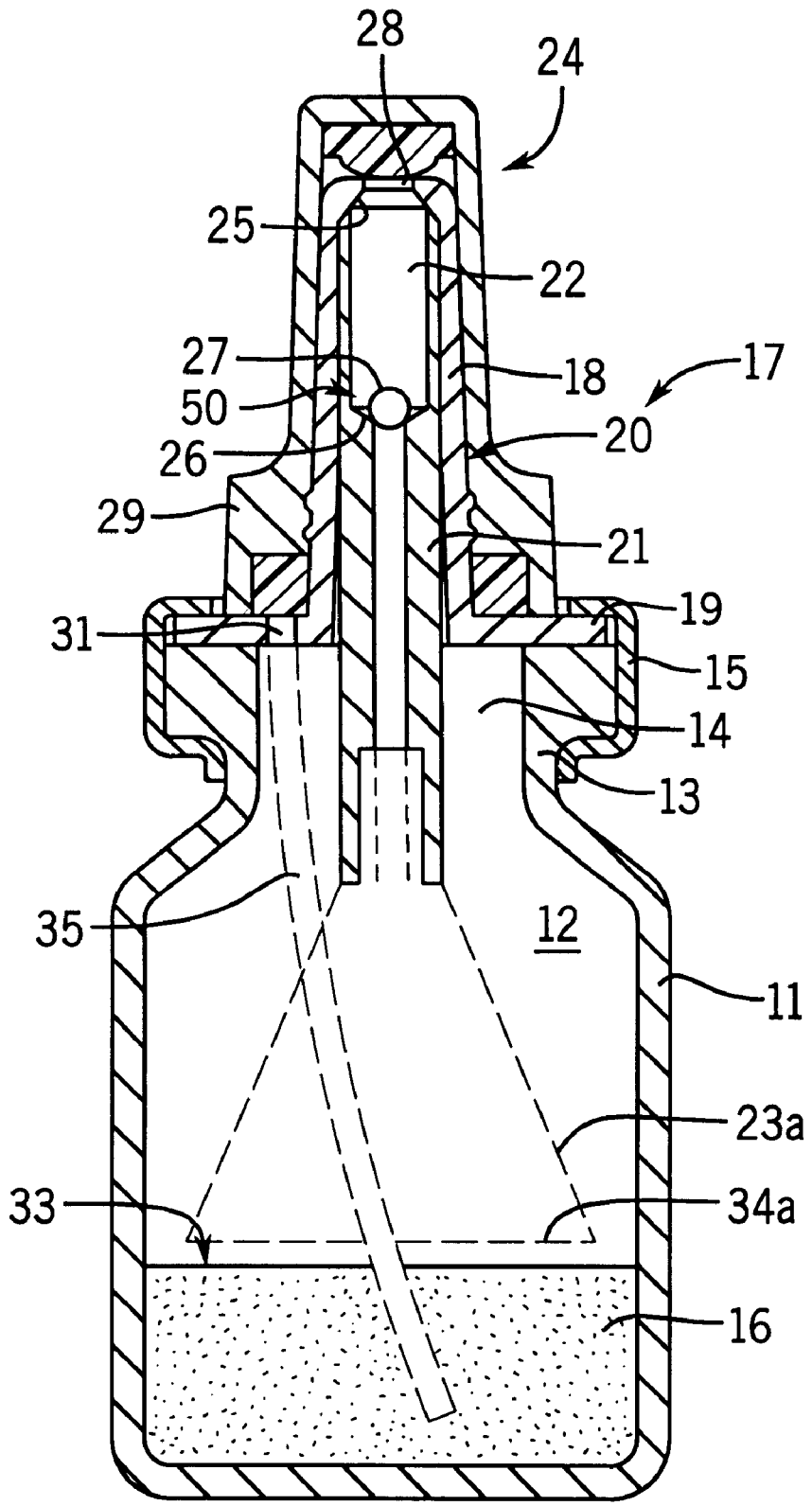
FIG. 1a is a vertical section identical with that of FIG. 1 except for a different construction of the suction tube.

At its upper end close to the aperture 28, the casing forms a valve seat 25 of a closure 24. The discharge channel has over a considerable distance of its length a diameter which is larger than the ball 27, so that a flow space having a cross-section 45 surrounding the valve body 27 is formed. At the end of the widened discharge channel 22 opposite to the valve seat 25 a further valve seat 26 is provided, on which rests the valve body 27 in its rest position to seal the discharge channel. From said valve seat a suction tube 23, having a suction opening 34, extends into the container and into the powder up to close to the container bottom. As shown in FIG. 1a, the suction tube 23a can have the form of a funnel having its suction opening 34a in the vicinity of the powder surface 33.

A cap 29 is screwed onto a thread of the mouthpiece 18 and seals both the aperture 28 and a vent opening 31 extending through the flange 19 between the atmosphere and the container. The vent 31 can be provided in the flange 19 as a simple opening, but it is also possible to connect a tube 35 there. This vent tube 35 shown in dot-dash line form leads below the powder surface and has its opening there.

Figure 3:
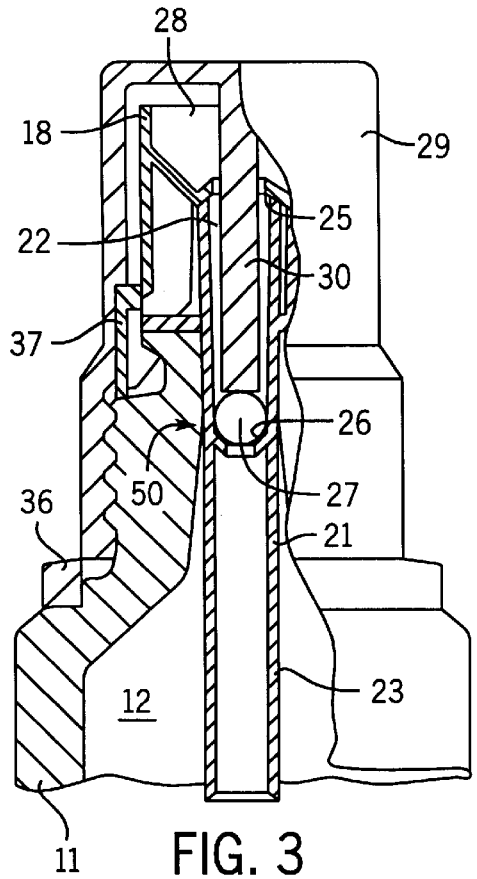
FIG. 3 is a detail view of a modified embodiment of FIGS. 1 and 2.

FIG. 3 shows on a larger scale a construction in which a centrally downwardly projecting, projection-forming pin 30 is fitted to the cap 29, and projects through the opening of the valve seat 25 and most of the widened discharge channel 22. The pin 30 is so dimensioned that in the screwed-on state the lower face of the pin 30 causes the valve body 27 to rest on the lower valve seat 26.

The cap 29 is also connected by an originality closure 36 to the container 11. The closure 36 is the form of a ring which is connected at predetermined breaking points to the cap 29, the closure 36 being separated from the container 11 during a first actuation.

There is also a child-resistant closure 37 of known construction, which allows only the cap 29 to be unscrewed from the casing 20 of the dosing device 17 after performing a specific sequence of operations, e.g. a pressing down of the cap, followed by a screwing movement.

In the vicinity of the rest position 50, the discharge channel 22 is not much wider than the diameter of the valve body 27, but then widens conically. This leads to a reliable acceleration of the valve body and a slower discharge start. In order to obtain other operational requirements a different discharge channel design can be provided.

Unlike FIGS. 1 and 2, the mouthpiece 18 in FIG. 3 is not in the form of a nose adaptor, but instead is intended to be received in the mouth and through it suction can then take place. Otherwise, the construction is substantially identical to that according to FIGS. 1 and 2.

Figure 4:
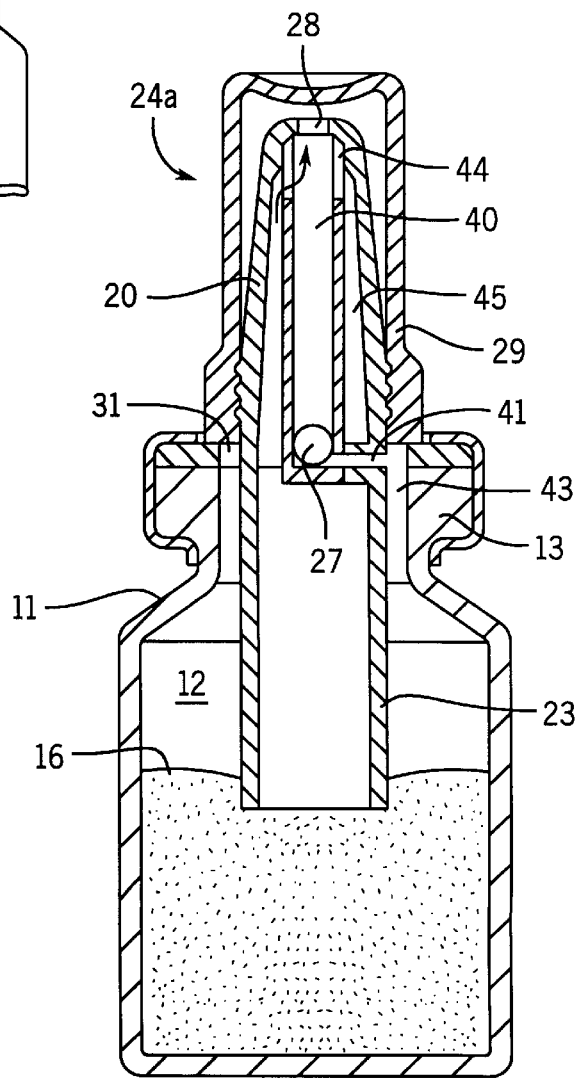
FIG. 4 is a vertical section view of another embodiment operating according to a suction principle in the same representation form.
Figure 5:
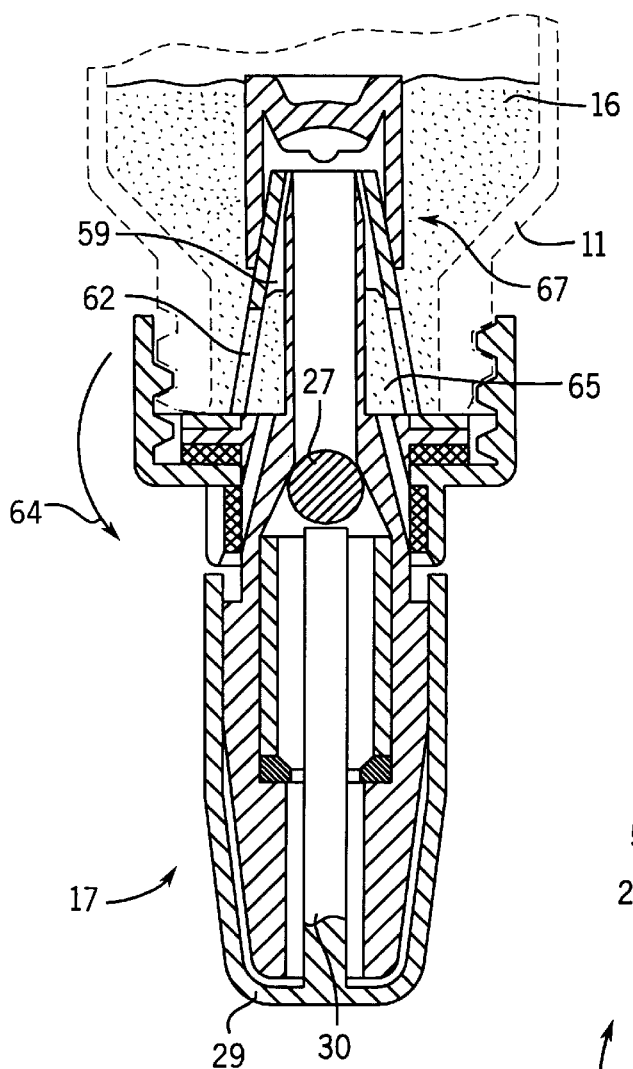
FIGS. 5–8 are vertical sections though a dosing device with pre-dosing abilities, shown in four functional positions.

This also applies for the construction according to FIG. 4, in which a closure of an actuation type is shown. Here again the closure 24a is provided in the form of a valve seat 25 at the upper end of the mouthpiece 18, which is constructed as a nose adaptor. The valve body 27 is constructed as a ball and provided at the end of a closure body channel 40, which projects inwardly into the casing 20, but it is not intended that the medium, or at least the main quantity thereof, flows therethrough. The valve body 27 is located at the end of the closure body channel 40 and largely fills its inner diameter, so that it can be moved therein in much the same way as a piston. At the lower end, i.e. on the underside of the valve body 27, a connecting opening 41 is provided, which in the present case projects through the very large diameter suction tube 23 into an annular clearance 43, which extends the vent channel 31 and bounds the inner circumference of the bottle neck 13.

In the upper part of the closure body channel 40, in its otherwise closed outer wall, slots 44 are provided through which the medium flowing in the annular clearance 45 between the inner wall of the casing 20 and the closure body channel 40 flows to the aperture 28 using the upper part of the closure body channel 40.

In the construction according to FIG. 1, for use purposes, the cap 29 is unscrewed and removed, so that the discharge channel 22 is free above the aperture 28. The dosing device can now be fitted to a body opening; e.g., the mouthpiece 18 can be inserted in a nostril.

If the user now inhales through the nostril, a flow is produced in the discharge channel 22 and the suction tube 23 connected thereto. The valve body 27 located in its starting position 50 (FIG. 1) at rest on the lower valve seat 26 lifts off from the latter and a flow around it can occur, because the discharge channel 22 is widened in comparison with the external diameter of the valve body 27. Through the suction tube 23 air is sucked out of the container and in the case of the wide, funnel-shaped suction opening 24 whirls up powder from the surface, which is mixed with the suction air and consequently penetrates as an air/powder dispersion or a solid aerosol into the corresponding body cavity of the user and can there exert its medical action. The construction with a suction tube extending to the container bottom is mainly provided with those powders which are themselves very loose and can therefore easily be brought into such an aerosol form.

When using a ventilation tube 35 the air flowing through the ventilation channel 31 into the container is used for replacing the withdrawn air and flows directly under the surface of the powder which ensures a uniform distribution of the air, even with the occurrence of turbulence.

Following the start of suction, a force exerted on the valve body 27 is produced by a difference in pressures above and below said valve body 27. The pressure difference is in turn dependent on the throttling in the flow around the valve body 27 and also on the flow rate. As a result, the valve body 27 moves upwards in the discharge channel 22. When it has traversed its movement path between the two valve seats 25, 26, it reaches and engages the closed position 51 (FIG. 2) against the upper valve seat 25 of the closure 24 and therefore seals the discharge channel 22 against the suction action.

Therefore, the user can only inhale that quantity of the medium (air/solid dispersion) that flows past it through the discharge channel 22 during the time in which the valve body 27 moves upwards. As the speed of the valve body 27 is determined by the flow rate, the dosage quantity remains relatively constant, even when the suction level differs. In the case of a higher suction rate, the quantity per time unit is greater, but the dosage time is shorter. Thus, there is a certain automatic control of the dosage quantity.

There is a corresponding function with the construction according to FIG. 3. For removing the cap here, it is first necessary to break open the originality closure 36 and then release the child-resistant closure 37. The pin 30 then frees the valve body previously blocked in the starting position and directly closing the valve seat 26. In this case, suction takes place via the mouth and for this purpose the mouthpiece has a corresponding design.

In the construction according to FIG. 4, the medium flows around the closure body channel 40 and through the slots 44 into the closure body channel and through the opening into the valve seat 25. Thus, in the closure body channel 40 a vacuum is produced, which sucks upwards the valve body 27 therein. Air flows in via the opening 42 from the annular clearance 43, said air penetrating the vent channel 31. However, it is also possible to provide the opening 42 in the bottom of the sleeve-like closure body channel 40, so that dispersions penetrate said channel 40, although only in a small quantity.

After traversing the path between the lower rest position of the valve body 27 and its upper closure position on the valve seat 25, the flow is interrupted and therefore the dosage is ended.

The time lag that allows the dosage is, in the illustrated embodiments, determined by the time required in the valve body 27 to cover the delay path between its rest position (in FIGS. 1 and 2 on the rest valve seat and in FIG. 3 on the bottom of the closure body channel) to the closure valve seat 25. This time could also be differently determined, rendered uniform or further delayed, e.g. by mechanical or other means. For example, consideration could be given to making the valve body run on a steep thread, which also performs a rotary movement for extending the dosage time. Other drive means for the valve body 25 are also possible. The valve body 27 is admittedly preferably a ball, because this is the easiest as regards manufacture and use. However, some other valve body shape could also be used, e.g. a valve body with a central pin and two conical or spherical ends, which projects through an opening and whose ends cooperate with valve seats positioned on both sides of the opening. The pin length then determines the delay path.

The dosing device as described herein is particularly advantageous for use in powder/air dispersions, preferably with those devices operating with suction from the outside. With said devices dosing represents a particular problem, because there is no feed device for the medium in the dosing device, such as, for example, a pump. However, it is also possible to use the dosing device in other apparatuses, for example, following a liquid atomizer. This can be important in an apparatus operating with a pressurized gas container.

The basic design of the dosing device according to FIGS. 5 to 8 corresponds to the design of FIGS. 1 and 2. Housing 20 of the dosing device 17 is fastened to the container 11 by a spigot nut **15*a*. Housing 20 has the form of a mouthpiece 18 having an inner discharge channel 22, which terminates in an outlet 28**.

A valve body 27 in form of a steel ball is axially movable in a part 56 of the discharge channel having an increased diameter. Both of its final positions start position 50 and closure position 51 are defined by valve seats 25, 26.

Valve seat 25 is provided at a valve seat ring 57 consisting of plastic material with magnetic properties. Plastic materials of a known type having magnetic particles incorporated therein can be used.

A suction tube 23 projects from the housing 20 into the container 11. Suction tube 23 is connected at its one end to valve seat 26 and terminates at its other end in an opening 34 which is surrounded by a conical tubular portion 58. A ring channel 59 formed between suction tube 23 and tubular portion 58 narrows conically in a direction of the opening 34 thereby forming a nozzle. It is directed to a bowl-shaped bottom 60 of a pre-chamber 67, which defines a medium receiver 61 on which the powder-shaped medium 16 is collected before it will be atomized by whirling up in the air. The tubular portion 58 is provided in its upper part (FIG. 6) with apertures 62, through which an accumulation chamber 65 at the upper end of the ring channel 59 is connected with the interior 12 of the container 11.

The spigot nut **15*a* and the housing 20 have several venting channels 31 at their circumference, which connect the interior 12 with the atmosphere. A ring filter 63 surrounds the outer apertures of the venting openings 31, and prevents contamination of the medium 16** by entry of airborne infectious material from the outside.

Cap 29 has, as described with reference to FIG. 3, a central pin-like projection 30 projecting through the discharge channel 22 to the valve seat 26.

The dosing device 17 is designed to be operated by means of suction applied by the mouth or the nose of a person. It is, however, possible to use an air pump (not shown) which may be provided in or adjacent to the container, which operates the discharge by means of an air stream.

Before starting an operation cycle the dosing device is in the position shown in FIG. 6. Cap 29 is put on the mouth piece and the pin 30 holds the valve ball 27 on valve seat 26, i.e. in the start position 50. To start the operation the dosing device 17 is turned about 180° by tilting according to arrow 64 into an overhead position shown in FIG. 5. This causes medium 16 to fall into the neck of the container 11 and to fill the accumulation chamber 65, which is formed in the upper part of ring channel 59 adjacent to the apertures 62. The filling of the accumulation chamber 65 is limited by the angle of repose for the medium. Medium 16 which may be still in the pre-chamber 67 is prevented from falling out of the discharge channel by the valve ball 27 fixed on the valve seat 26 by pin 30.

Figure 6:
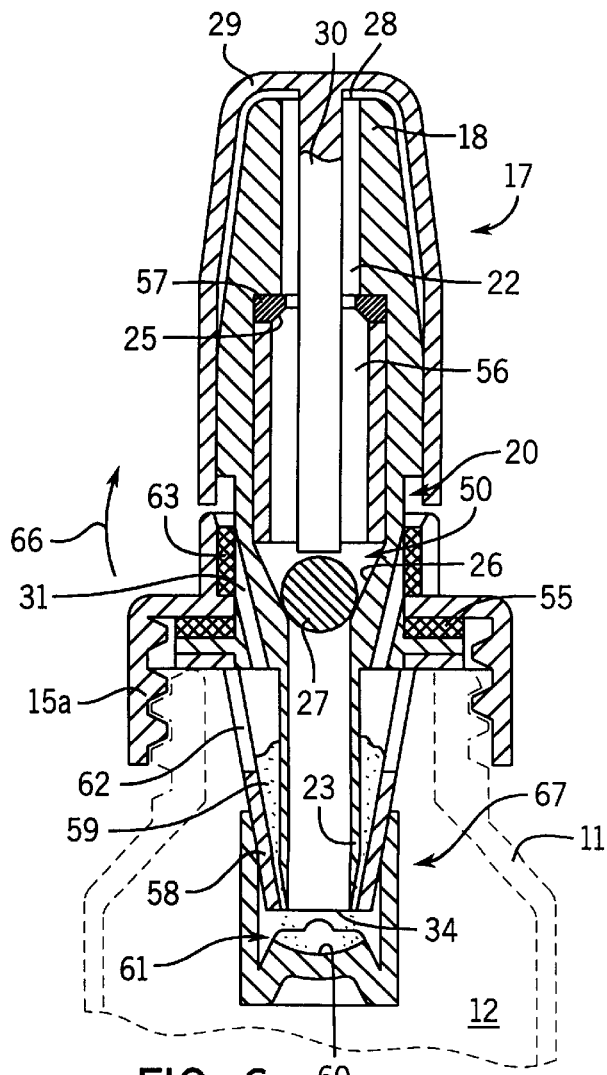

Thereafter, the dosing device 11 will be turned back into the upright position (FIG. 6) by tilting it according to arrow 66. Most of the medium 16 falls back into the container 11 except the portion which falls from the accumulation chamber 65 into the conical ring channel 59. It flows down from there to the pre-chamber 67 and on the bowl-shaped bottom 60 of the medium receiver 61 as a metered quantity.

Figure 7:
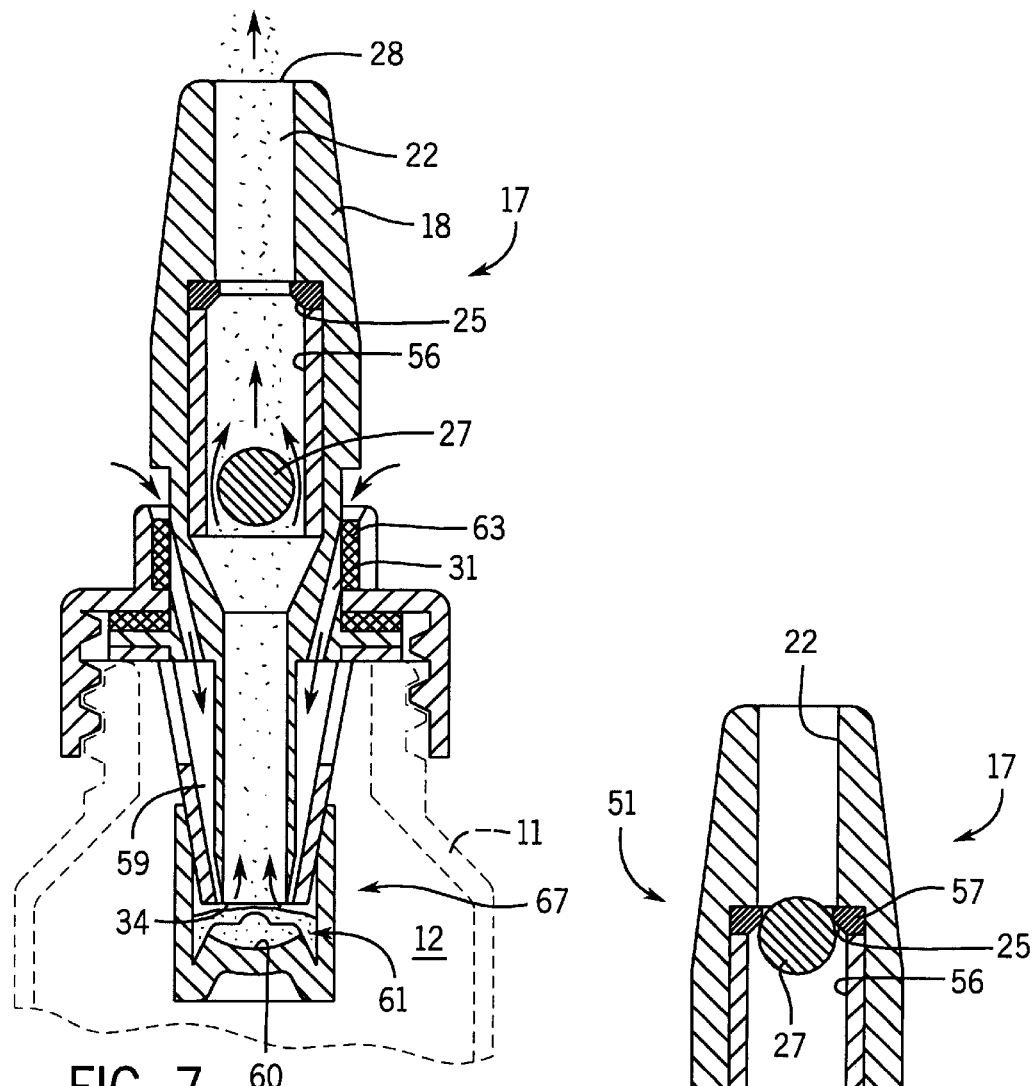

The discharge operation is started by suction at mouth piece 18 (FIG. 7). The lower valve is opened under the action of the suction. The valve ball 27 lifts from valve seat 26 and the ball moves upwardly in part 56 of the discharge channel 22 against its gravity, caused by the drag of the medium/air-mixture flowing through the gap between the ball and channel. This causes air to flow through filter 63 and venting openings 31 into the container 11 and via ring channel 59 into pre-chamber 67. The ring nozzle shape of the mouth of ring channel 59 which surrounds the mouth of the suction tube 34, helps to whirl up the medium 16 lying on the medium receiver 61 in the air stream. It produces a uniform mixture of powder and air which is discharged via suction tube and discharge channel 22. Thereby, a very good and uniform aerosol is produced. The collection of a defined amount of medium in the pre-chamber assures a pre-dosing of the medium. Thereby, any intentional or unintentional manipulation of operation is prevented and it is assured that the dosing is sufficiently defined.

Figure 8:
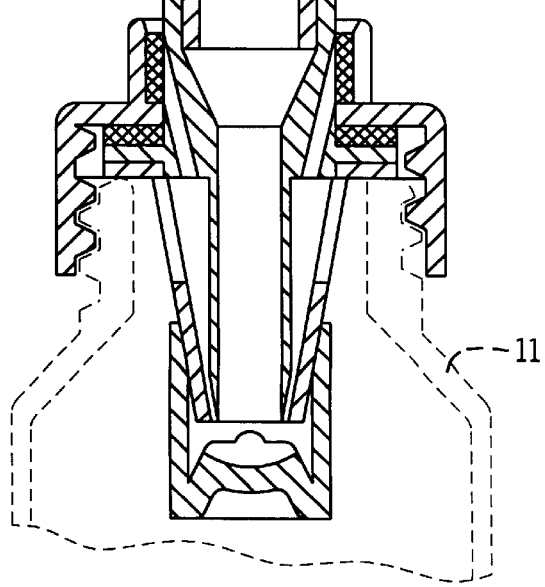

If the valve ball 27 reaches valve seat 25 under the action of the air stream, i.e. its closure position 51, the discharge is suddenly ended (FIG. 8). The valve ball 27 stays at the valve seat 25 under the action of the magnetic force of ring 57 and also as a result of suction from the outside or pressure from the inside of the container. This prevents a person from operating the device again, which otherwise may be possible after the ball has again fallen down in the discharge channel. The magnetic action provides, therefore, a holding means for the closure. It could also consist or include mechanical means, e.g. flaps of plastic material projecting into the discharge channel.

For starting a new operation cycle, the person must again put the cap 29 on the mouth piece to push the valve ball 27 from valve seat 25 using pin 30 and to bring the valve body 27 again into its start position 50.

The embodiment of FIGS. 5 to 8 assures a very reliable and uniform discharge with pre-dosing and prevents unintentional double operation. It further assures sterilized storage of the medium between operation cycles.

I claim:

1. A dosing and discharging device for flowable media, comprising a housing containing a discharge channel having an outlet opening channel, through which channel a stream of media flows to the outlet opening during discharge, closure means in said discharge channel for interrupting discharge of the medium through said discharge channel, when the closure means are in a closure position, the closure means being movable from a start position, in which the closure means rests at start of discharge, to the closure position under the action of the stream, whereby the discharge is terminated after a time lag controlled by the movement of the closure means from said start position to said closure position.

2. Device according to claim 1, wherein the closure means have a valve body cooperating with at least one valve seat.

3. Device according to claim 2, wherein the discharge channel has an inner wall, a throttling gap being provided between the valve body and said inner wall of the discharge channel, whereby said stream is throttled while flowing through said discharge channel.

4. Device according to claim 1, wherein the closure means maintains the discharge channel closed after operation of the device.

5. Device according to claim 4, further comprising holding means for holding the closure means in said closure position until being removed therefrom by mechanical opening means.

6. Device according to claim 5, wherein the holding means include a magnetic part.

7. Device according to claim 5, wherein the opening means include a projection of a closure cap to be placed over the outlet opening.

8. Device according to claim 2, wherein the valve body is urged, counter to direction of the stream by gravity and moved in stream direction by drag of the medium flowing round it.

9. Device according to claim 3, wherein the throttling gap formed between the valve body and the discharge channel is variable over the length of the discharge channel between the starting and closed positions.

10. Device according to claim 2, wherein the valve body is movable by suction produced by the flow in the discharge channel from a position outside the discharge channel into the closed position.

11. Device according to claim 1, wherein the device is an inhaler for powder/air dispersion containing a mouthpiece for suction of dispersion from a powder container, the discharge channel being located between a suction opening in the container and the mouthpiece and wherein there is at least one ventilation channel leading into the container.

12. Device according to claim 2, further comprising a closure cap to cover the outlet opening of the discharge channel, the closure cap having a projection projecting into the discharge channel and holding the valve body on a start position valve seat.

* * * * *